United States Patent

Bennett, II

[11] Patent Number: 5,846,487
[45] Date of Patent: Dec. 8, 1998

[54] SPECIMEN CARTRIDGE

[76] Inventor: Edward R. Bennett, II, 3925 Madison Ave., Greensboro, N.C. 27410

[21] Appl. No.: 755,834

[22] Filed: Nov. 26, 1996

[51] Int. Cl.$^6$ ..................................................... G01N 1/00
[52] U.S. Cl. .................. 422/58; 422/56; 422/61; 422/99; 422/102; 422/104
[58] Field of Search .................. 422/56, 58, 61, 422/99, 101, 102, 104

[56] References Cited

U.S. PATENT DOCUMENTS

| | | | |
|---|---|---|---|
| D. 245,118 | 7/1977 | Heaton | D24/32 |
| 4,092,115 | 5/1978 | Rupe et al. | 422/56 X |
| 4,229,813 | 10/1980 | Lilly et al. | 422/56 X |
| 4,250,257 | 2/1981 | Lee et al. | 422/56 X |
| 4,608,231 | 8/1986 | Witty et al. | 422/61 |
| 4,774,054 | 9/1988 | Charlton et al. | 422/56 |
| 4,857,453 | 8/1989 | Ullman et al. | 435/7 |
| 5,047,206 | 9/1991 | Dombrowski | 422/56 |
| 5,096,669 | 3/1992 | Lauks et al. | 422/61 |
| 5,108,927 | 4/1992 | Dorn | 435/296 |
| 5,160,021 | 11/1992 | Sibley et al. | 206/204 |
| 5,238,652 | 8/1993 | Sun et al. | 422/61 |
| 5,260,221 | 11/1993 | Ramel et al. | 436/169 |
| 5,306,466 | 4/1994 | Goldsmith | 422/58 |
| 5,352,411 | 10/1994 | Khuri | 422/58 |
| 5,425,915 | 6/1995 | Phillips et al. | 422/58 |
| 5,427,743 | 6/1995 | Markin | 422/104 |
| 5,431,884 | 7/1995 | McDonough et al. | 422/101 |
| 5,597,532 | 1/1997 | Connolly | 422/58 |
| 5,656,448 | 8/1997 | Kang et al. | 435/7.94 |

*Primary Examiner*—Harold Y. Pyon

[57] ABSTRACT

A specimen cartridge for biological materials is formed from unbreakable materials, such as cardboard or synthetic polymers. The specimen cartridge includes a handle, a receptor attached to the handle, and an outer housing. The receptor and handle are slidable relative to the outer housing which may include a bar-coding label and a security tape. The outer housing and receptor fit snugly together to provide a liquid-tight, leak-proof seal to prevent the escape of any biological materials from the receptor. Thus, the specimen cartridge minimizes the risk of contamination caused by the storage and transport of potentially hazardous biological materials. Further, the outer housing and receptor are formed of shatter-proof materials, also to prevent contamination. A carrying case is adapted for safely and securely transporting and testing a plurality of specimen cartridges.

8 Claims, 4 Drawing Sheets

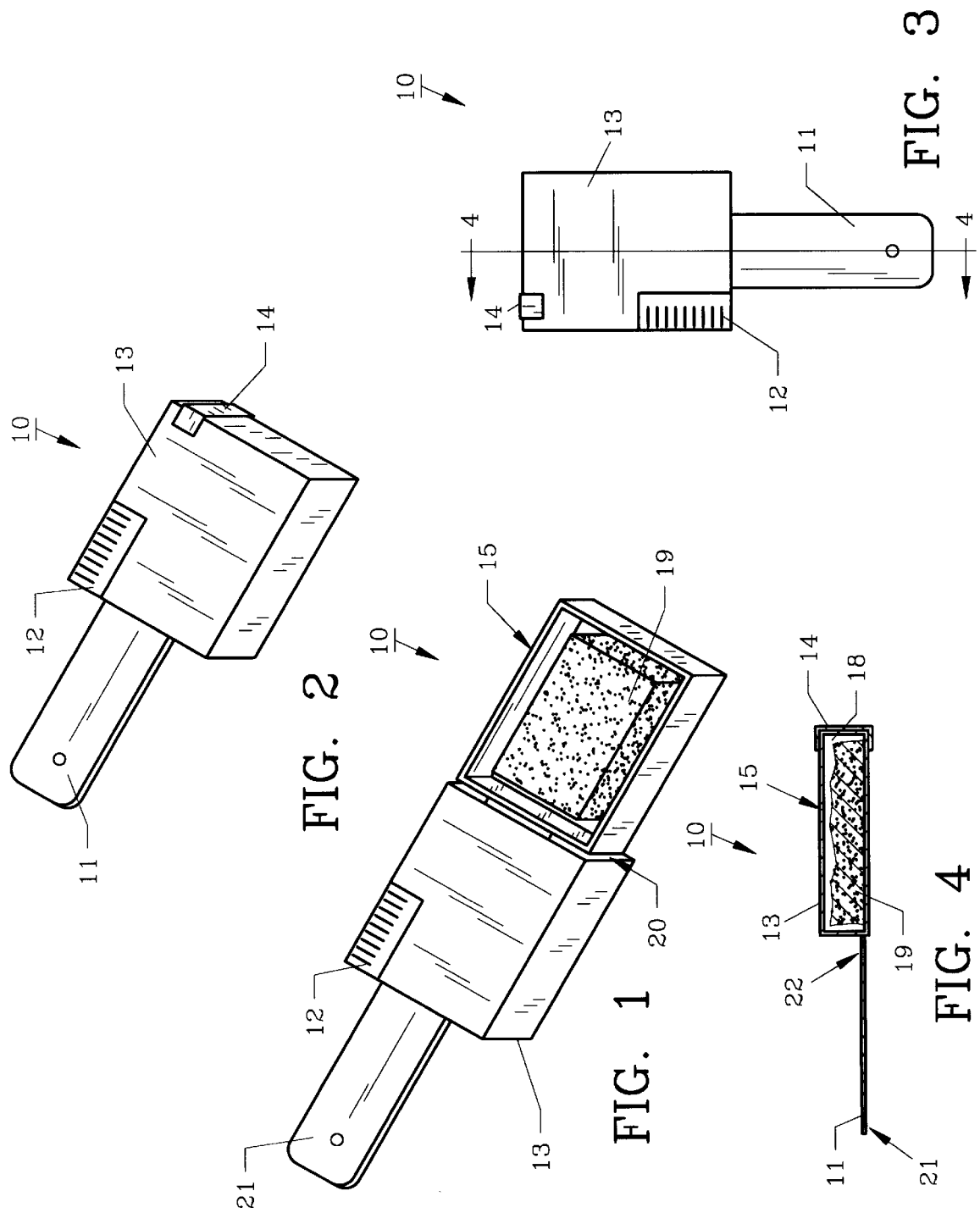

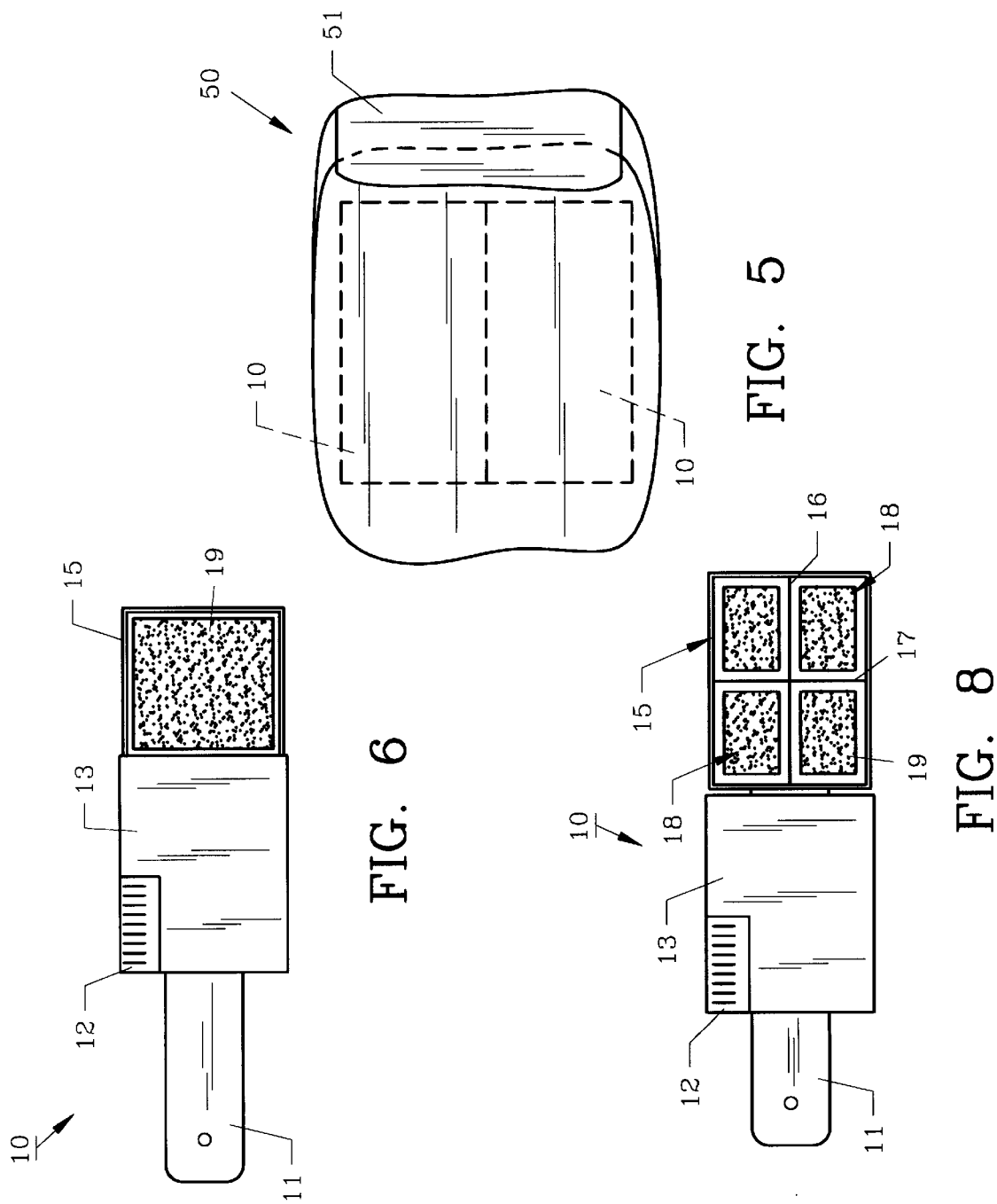

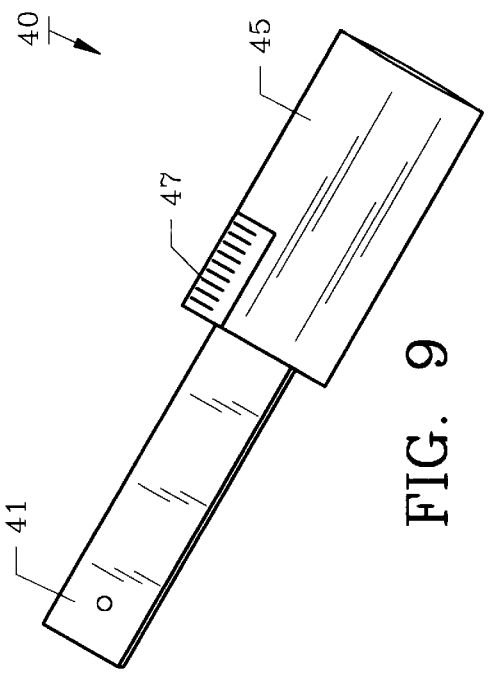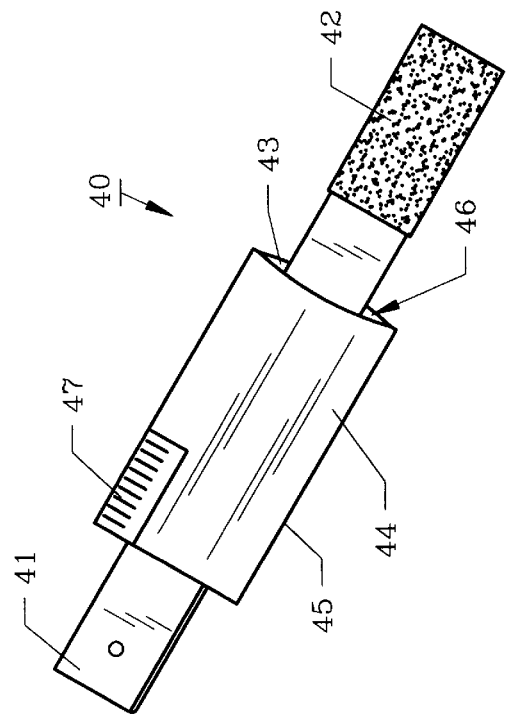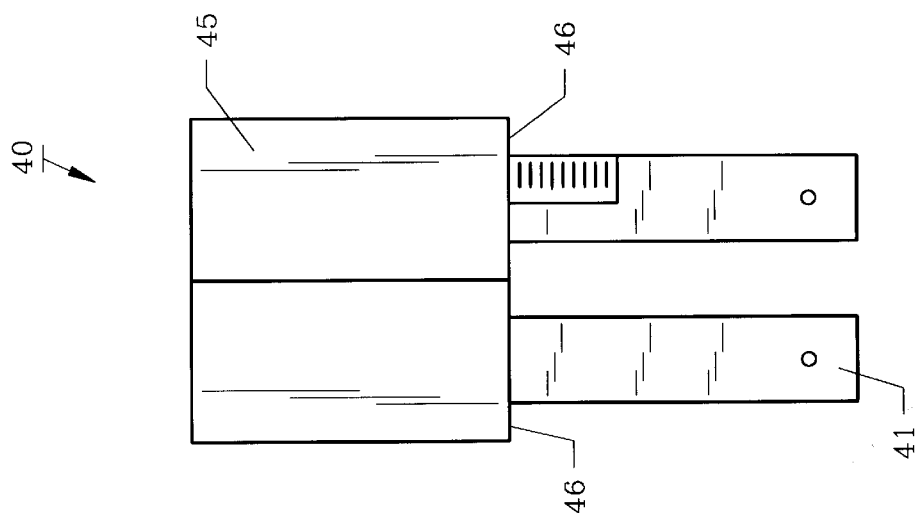

SPECIMEN CARTRIDGE

BACKGROUND OF THE INVENTION

1. Field of the Invention

The instant invention discloses a cartridge for storing and transporting biological specimens, such as blood, urine, or other fluids. The invention is primarily applicable to the diagnostic and analytical fields of medicine, especially for drug and blood testing applications. Also disclosed is a portable rack adapted for testing or transporting a plurality of the specimen cartridges.

2. Description Of Related Art And Objectives Of The Invention

Recent years have seen a substantial increase in the number of individuals being tested for drug use and blood-borne disease. With the increase in testing comes an increasing demand for devices and methods that allow safe, efficient, and economical storage and treatment of biological specimens, such as blood and urine. Also, the sheer number of blood and urine tests now being conducted demands that these devices and methods support accurate tracking and processing, especially by automated systems.

The art teaches the storage and transportation of biological specimens in hollow cylindrical devices, such as test tubes, that are manufactured from glass or other breakable materials. Because of their composition and shape, these devices suffer from several disadvantages. First, glass test tubes are notoriously susceptible to breakage, and if these test tubes contain hazardous biological specimens, such breakage can contaminate the surroundings. Second, cylindrical objects can be difficult to control while processing the biological material. Standard specimen containers having a wide opening are susceptible to spillage or leakage. Often, medical personnel must employ racks or stands to stabilize the test tubes and to prevent them from rolling about or falling from a work area.

These disadvantages of prior art devices motivated the instant invention. Thus, a first objective of the invention is to provide a specimen cartridge that is not susceptible to breakage or leaks.

A second objective of the invention is to provide a specimen cartridge that is not prone to roll about a work area.

A third objective of the invention is to provide a specimen cartridge comprising a handle, a receptor mounted to the handle, and an outer housing, wherein the receptor slides into and out of sealing engagement with the outer housing.

A fourth objective of the invention is to provide a specimen cartridge comprising a handle, a receptor mounted to the handle, and an envelope, wherein the receptor slides into and out of sealing engagement with the envelope. An opening is provided in the handle for storage or handling purposes.

A fifth objective of the invention is to provide a specimen cartridge that defines a plurality of channels adapted for carrying a plurality of receptors.

A sixth objective of the invention is to provide a portable storage case adapted for transporting or testing a plurality of the specimen cartridges of the invention.

A seventh objective of the invention is to provide a method for storing, transporting, securing and tracking biological specimens that supports automated processing.

SUMMARY OF THE INVENTION

The above objectives are met by a specimen cartridge formed from unbreakable material such as cardboard treated with a wax, polymer, or other suitable material, or a high-impact polymer. The specimen cartridge comprises a handle, a receptor attached to the handle, and an outer housing. The receptor and handle are slidable relative to the outer housing between an open position, in which the receptor is accessible, and a closed position, in which the receptor is sealed inside the outer housing. The specimen cartridge comprises a bar-coded label, or other identification means, and also comprises a security tape for tamper identification. Finally, the specimen cartridge has a generally planar configuration that is not susceptible to rolling.

In use, the receptor is slid relative to the outer housing until the receptor is fully exposed. Then, biological specimens are placed into the receptor. Finally, the receptor is slid relative to the outer housing until the receptor is fully sealed inside the outer housing. The specimen cartridge can then be scanned into an automated tracking system by reading the bar code label. Also, the specimen cartridge can be protected against tampering by applying a suitable security tape across the outer housing and receptor or a security seal can be integrally molded thereon during manufacture.

The outer housing and receptor fit snugly together to provide a liquid-tight, leak-proof seal to prevent the escape of any biological materials. Thus, the specimen cartridge minimizes the risk of inadvertent contamination caused by the storage and transport of potentially hazardous biological materials. Further, the outer housing and receptor are formed of shatter-proof materials, also to prevent contamination.

Optionally, the receptor may be sub-divided into a plurality of compartments, so that a plurality of biological specimens may be stored in one receptor. Also, the outer housing of a specimen cartridge may define a plurality of channels, into which a plurality of receptors may be inserted. A carrying case adapted for safely and securely transporting a plurality of the specimen cartridges is also disclosed.

BRIEF DESCRIPTION OF THE DRAWINGS

FIG. 1 is a perspective view of the preferred embodiment of the invention, in the open position;

FIG. 2 is a perspective view of the preferred embodiment of the invention, in the closed position;

FIG. 3 is a top plan view of the device shown in FIG. 1;

FIG. 4 is a cross-sectional view taken along the line 4—4 in FIG. 3;

FIG. 5 is a top plan view of the preferred embodiment placed in a pouch;

FIG. 6 is a top plan view of the device shown in FIG. 1, in the partially-open position;

FIG. 8 is a top plan view of another alternative embodiment of the device shown in FIG. 1, in the open position;

FIG. 9 is a top plan view of another alternative embodiment of the invention, in the closed position;

FIG. 10 is a top plan view of the device shown in FIG. 9, in the open position;

FIG. 11 is an alternative embodiment of the device shown in FIG. 9; and

DESCRIPTION OF THE PREFERRED EMBODIMENT

Figure 7:
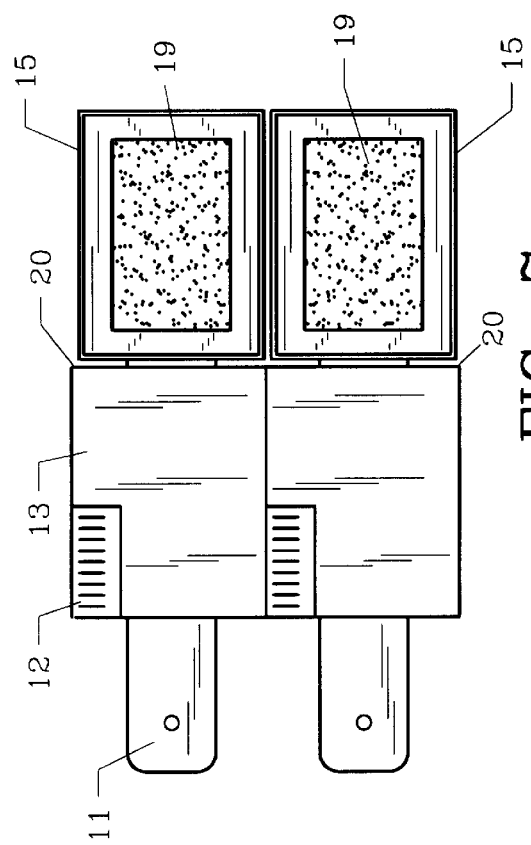
FIG. 7 is a top plan view of an alternative embodiment of the invention, in the open position.

The preferred embodiment of the invention consists of a single specimen cartridge comprising a receptor attached to an extending handle and slidably positionable inside an outer housing. The receptor is a walled container having an open top, and having an absorbing means positioned inside the container.

The preferred method of the invention comprises sliding the receptor relative to the outer housing until the receptor is fully exposed, placing biological specimens into the receptor, and sliding the receptor relative to the outer housing until the receptor is fully sealed inside the outer housing. The specimen cartridge can then be scanned into an automated tracking system by reading the bar code label. Also, the specimen cartridge can be protected against tampering by applying a suitable security tape across the outer housing and receptor.

DETAILED DESCRIPTION OF THE DRAWINGS AND OPERATION OF THE INVENTION

Turning now to the drawings, FIGS. 1, 2, 3, 4, and 6 illustrate the preferred embodiment of the invention, specimen cartridge 10. FIG. 1 shows specimen cartridge 10 in the open position; FIG. 2 shows specimen cartridge 10 in the closed position; FIG. 3 is a top plan view of specimen cartridge 10; FIG. 4 is a cross-sectional view of specimen cartridge 10; and FIG. 6 shows specimen cartridge 10 in the partially-open position.

Handle 11 is elongated and includes two opposing ends 21 and 22 (shown in FIG. 4). Handle 11 may be formed of wood, metal, polymers, cardboard, or other relatively low-cost materials. To one end 22 of handle 11 is attached receptor 15. Receptor 15 is preferably a walled container having an open top. Absorbing means 19 may be placed inside receptor 15 and may comprise any material capable of absorbing blood, urine, or other biological fluids. Receptor 15 slidably engages outer housing 13, which serves as a removable container for receptor 15.

Outer housing 13 defines a channel 20, which slidably carries receptor 15. The outer dimensions of receptor 15 are approximately equal to the inner dimensions of channel 20. These approximately equal dimensions enable receptor 15 to fit snugly by frictional engagement into channel 20 of outer housing 13, which snug fit promotes a liquid-tight, leak-proof seal between receptor 15 and outer housing 13.

Outer housing 13 and receptor 15 are preferably formed from non-breakable materials, such as a treated cardboard or high-impact polymer. The most preferred material is medical-grade polypropylene. Because outer housing 13 and receptor 15 are formed from non-breakable materials, and because receptor 15 and outer housing 13 fit snugly together, the risk of hazardous biological materials escaping from specimen cartridge 10 is minimized.

To protect the contents of specimen cartridge 10, security tape 14 is placed across receptor 15 to provide means for detecting tampering of specimen cartridge 10. Also, bar code label 12 facilitates automated tracking of several specimen cartridges 10.

FIG. 5 illustrates specimen cartridge 10 placed inside pouch 50. Pouch 50 comprises a fluid-impervious metallic or polymeric material that can be either flexible or rigid. Flap 51 seals specimen carrier 10 inside pouch 50.

As shown in FIG. 8, receptor 15 can be partitioned by intermediate walls 16 and 17 to form a plurality of compartments 18 within receptor 15. Also, separate means 19 for absorbing liquid specimens can be placed inside the several compartments 18 thus formed. This structure allows a technician to place redundant samples of a given biological specimen within receptor 15 to accommodate repetitive testing.

As shown in FIG. 7, outer housing 13 can define a plurality of parallel channels 20. A separate receptor 15 can then be placed within each of the parallel channels 20. In this embodiment, a plurality of receptors 15 can be carried in outer housing 13.

FIGS. 9 and 10 show another embodiment of the invention, specimen cartridge 40. FIG. 9 shows specimen cartridge 40 in the closed position; FIG. 10 shows specimen cartridge 40 in the open position. Handle 41 is attached to receptor 42, consisting of a urine, blood or other fluid absorbent pad which fits within envelope 45. Envelope 45 includes top 44 and bottom 43, which are joined along their opposing sides to define opening 46, which slidably carries receptor 42. Opening 46 is sized to snugly, sealingly enclose receptor 42 by frictional engagement.

As shown in FIG. 11, envelope 45 can define a plurality of openings 46. A separate receptor 42 can then be placed within each of the openings 46. In this embodiment, a plurality of receptors 42 can be carried in envelope 45 which may number two or more joined together by various means.

Figure 12:
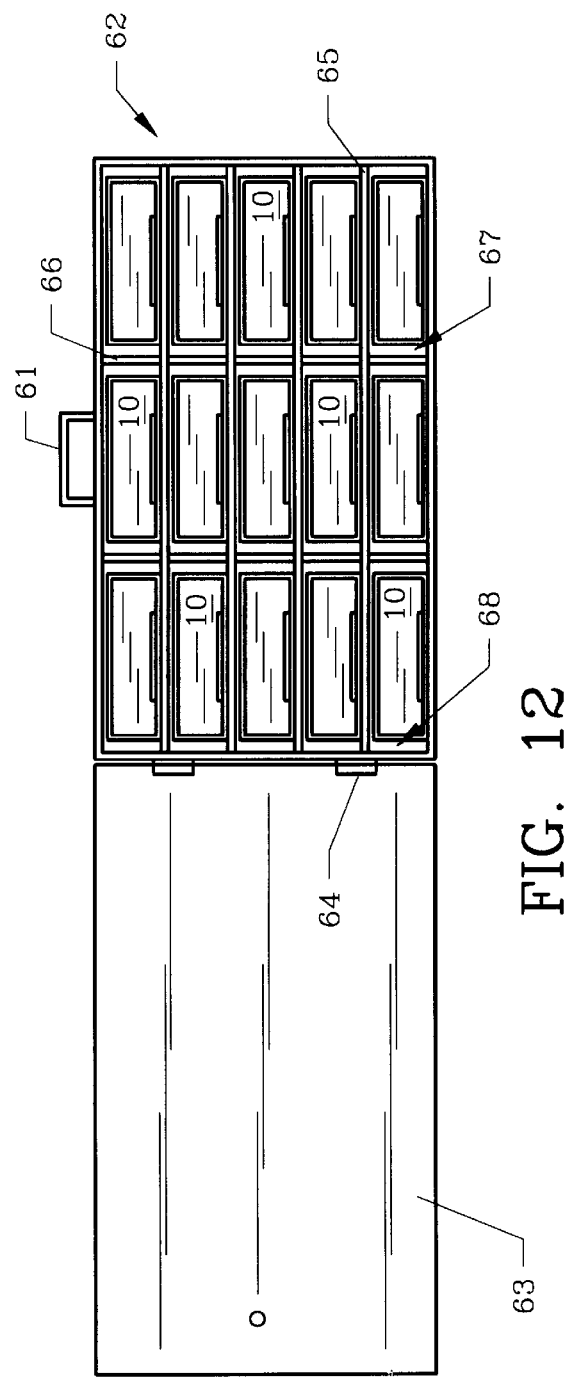
FIG. 12 is an elevation view of the carrying case of the invention.

Carrying case 60, shown in FIG. 12, includes cabinet 62, door 63, shelf 65, and divider 66. Door 63 is attached to cabinet 62 by hinge 64. Other outer covers may also be affixed to cabinet 62 such as by sliding or by plastic film covering. Handle 61 is joined to the top of cabinet 62 which defines interior space 68, and one or more shelves 65 and dividers 66 can be arranged perpendicularly to partition interior space 68 into a plurality of storage spaces 67. Specimen cartridges 10 are inserted into storage spaces 67 for transport. Carrying case 60 is preferably formed of a high-impact polymer. Door 63 swings from an open position, allowing access to interior space 68, to a closed position, sealing interior space 68. Carrying case 60 also includes means for identifying storage spaces 67, such as bar coding or by numbered labels.

The illustrations and examples provided herein are for explanatory purposes and are not intended to limit the scope of the appended claims as those skilled in the art will vary the materials used and the construction. Other collection needs can be met, e.g., environmental water and soil testing can also utilize the advantages of the described embodiments.

I claim:

1. A specimen cartridge comprising:
   (a) an elongated handle;
   (b) a receptor, said receptor attached to said handle;
   (c) an outer housing, said outer housing contiguous to said receptor, said outer housing slidable longitudinally of said handle between open and closed positions so as to sealingly engage said receptor within said housing in said closed position, said handle generally exterior of said housing;
   (d) means for absorbing biological materials, said absorbing means positioned within said receptor; whereby a user may grasp said handle in both of said open or closed positions for manipulation or transportation purposes in both said open or closed positions; and (e) a plurality of receptors, and wherein said outer housing defines a plurality of channels, one each of the receptors slidably, sealingly positioned within one each of the channels.

2. The specimen cartridge of claim 1, further comprising means for identifying the same, said identifying means positioned on said outer housing.

3. The specimen cartridge of claim 1, further comprising means for identifying said receptor, said identifying means positioned on said handle.

4. The specimen cartridge of claim 1, wherein said specimen cartridge is formed of treated cardboard.

5. The specimen cartridge of claim 1, wherein said handle is formed of a polymer.

6. The specimen cartridge of claim 1, wherein said receptor is partitioned to form a plurality of compartments therewithin.

7. The specimen cartridge of claim 1, further comprising means for detecting tampering, said tampering detection means affixed to said outer housing.

8. The specimen cartridge of claim 7, wherein said tampering detection means comprises a security tape.

* * * * *